United States Patent
Ohnishi et al.

(10) Patent No.: US 8,153,551 B2
(45) Date of Patent: Apr. 10, 2012

(54) OPTICAL ISOMER SEPARATING FILLER

(75) Inventors: Atsushi Ohnishi, Himeji (JP); Yutaka Isobe, Myoko (JP)

(73) Assignee: Daicel Chemical Industries, Ltd., Osaka-Shi, Osaka (JP)

( * ) Notice: Subject to any disclaimer, the term of this patent is extended or adjusted under 35 U.S.C. 154(b) by 119 days.

(21) Appl. No.: 12/449,274

(22) PCT Filed: Feb. 22, 2008

(86) PCT No.: PCT/JP2008/053584
§ 371 (c)(1),
(2), (4) Date: Jul. 30, 2009

(87) PCT Pub. No.: WO2008/102920
PCT Pub. Date: Aug. 28, 2008

(65) Prior Publication Data
US 2010/0041878 A1 Feb. 18, 2010

(30) Foreign Application Priority Data
Feb. 23, 2007 (JP) ................. 2007-044672

(51) Int. Cl.
*B01J 20/22* (2006.01)
*B01J 20/24* (2006.01)
*B01J 20/26* (2006.01)
(52) U.S. Cl. .......... 502/404; 502/400; 502/401
(58) Field of Classification Search .......... 502/400, 502/401, 404
See application file for complete search history.

(56) References Cited

U.S. PATENT DOCUMENTS

| | | | |
|---|---|---|---|
| 4,861,872 A | 8/1989 | Okamoto et al. | |
| 5,679,572 A | 10/1997 | Okamoto et al. | |
| 5,965,026 A * | 10/1999 | Oda et al. ............. | 210/635 |
| RE38,435 E | 2/2004 | Okamoto et al. | |

FOREIGN PATENT DOCUMENTS

| | | |
|---|---|---|
| EP | 0 527 235 A1 | 2/1993 |
| EP | 1 422 521 A1 | 5/2004 |
| JP | 61-233633 | 10/1986 |
| JP | 2002-148247 A | 5/2002 |
| JP | 2005-315668 A | 11/2005 |
| WO | WO 97/04011 | 2/1997 |

OTHER PUBLICATIONS

Chankvetadze et al., "Enantioseparations Using Cellulose Tris(3,5-dichlorophenylcarbamate) During High-performance Liquid Chromatography with Analytical and Capillary Columns: Potential for Screening of Chiral Compounds." Combinatorial Chem. & High Throughput Screening (2000), 3, 497-508.*
Okamoto et al., "Chromatographic Resolution Xl, Controlled Chiral Recognition of Cellulose Triphenylcarbamate Derivatives Supported on Silica Gel." J. Chromatog., vol. 363 (1986), pp. 173-186.*
Form PCT/ISA/210 dated Mar. 25, 2008 (2 pages).
International Preliminary Report on Patentability dated Sep. 1, 2009.

* cited by examiner

*Primary Examiner* — Stuart Hendrickson
*Assistant Examiner* — Daniel Berns
(74) *Attorney, Agent, or Firm* — Flynn, Thiel, Boutell & Tanis, P.C.

(57) ABSTRACT

An optical isomer separating filler wherein a polysaccharide derivative is chemically bonded onto a support. This optical isomer separating filler is characterized in that the halogen content in the filler is 3.0 to 5.0%.

2 Claims, 6 Drawing Sheets

OPTICAL ISOMER SEPARATING FILLER

TECHNICAL FIELD

The present invention relates to an optical isomer separating filler having an excellent solvent resistance and separating ability, and more specifically, to an optical isomer separating filler in which a polysaccharide derivative is chemically bonded to a support, the optical isomer separating filler having the following characteristic: a halogen content in the filler is 3.0% to 5.0%.

BACKGROUND ART

In recent years, the importance of optically active compounds has been significantly growing in the fields of, for example, medicine, agricultural chemicals, food, flavors, and liquid crystals. In particular, in the field of medicine, the following facts have been known: only one optical isomer may show a pharmacological effect, there may be a difference in extent between the pharmacological effects of the optical isomers, or the pharmacological effects themselves may be different from each other. In view of such circumstances, it has been a serious problem to secure a needed optically active compound as inexpensively and stably as possible.

Under the above-mentioned need, a technique for separating optical isomers by high performance liquid chromatography (HPLC) is expected to be one method of securing only a needed optically active compound inexpensively and stably. It has been heretofore known that polysaccharide derivatives each have an excellent ability to separate optical isomers (for example, Patent Documents 1 and 2).

Optical isomer separating fillers comprising the polysaccharide derivative have the following characteristics: each kind of the fillers can separate a large number of optical isomers and is excellent in general-purpose property. However, not all the optical isomers that exist in the world can be separated with one kind of an optical isomer separating filler, so the filler and optical isomer separating filler as described below have been developed: a filler having a separating ability by which optical isomers that cannot be separated with existing fillers can be separated and an optical isomer separating filler having a separating characteristic different from those of the existing fillers.

The modification of a hydroxyl group or amino group of a polysaccharide with a compound having a characteristic structure has been performed as one approach to providing a filler having a separating ability and separating characteristic different from those of the existing fillers. For example, a filler using a halogen-substituted aromatic carbamate derivative of a polysaccharide obtained by modifying a hydroxyl group or amino group of the polysaccharide with an aromatic compound, a part of which is substituted with a halogen as an active ingredient, has been developed, and it has been revealed that the filler has a separating characteristic different from that of a non-halogen-substituted aromatic carbamate derivative of a polysaccharide (Patent Document 3).

In addition, the following approach has been performed: a solvent-resistant filler capable of using even a solvent that dissolves a polysaccharide derivative as a mobile phase is developed by chemically bonding the polysaccharide derivative to a support, or by crosslinking the molecules of the polysaccharide derivative carried by the support so that the filler may be applicable to an additionally wide range of separation conditions, and can separate optical isomers that cannot be separated with existing optical isomer separating fillers. In view of the foregoing, various solvent-resistant fillers have been developed. Examples of methods of chemically bonding a polysaccharide derivative to a support include: a method involving causing the support to carry the polysaccharide derivative physically and irradiating the resultant filler with light to immobilize the polysaccharide derivative chemically (Patent Document 4); a method involving chemically bonding a reducing terminal of the polysaccharide derivative to the support (Patent Document 5); and a method involving introducing a polymerizable group into each of the polysaccharide derivative and the support and copolymerizing the polysaccharide derivative and the support in the presence of a third component having a polymerizable group to chemically bond the polysaccharide derivative and the support (Patent Document 6).

As described above, optical isomer separating fillers having various separating abilities and separating characteristics have been developed. However, the fact remains that optical isomers that cannot be separated, even with various optical isomer separators, are still present, so the further development of an optical isomer separating filler having a separating ability and separating characteristic different from those of conventional products has been demanded with a view to enabling the separation of such optical isomers.

Patent Document 1: JP 60-142930 A

Patent Document 2: JP 63-178101 A

Patent Document 3: JP 61-233633 A

Patent Document 4: JP 11-510193 A

Patent Document 5: JP 07-138301 A

Patent Document 6: JP 2002-148247 A

DISCLOSURE OF THE INVENTION

Problems to be Solved by the Invention

An object of the present invention is to provide a solvent-resistant optical isomer separating filler having a unique separating characteristic different from those of existing optical isomer separators.

Means for Solving the Problems

That is, the present invention is as follows.

1. An optical isomer separating filler, which is obtained by chemically bonding a polysaccharide derivative onto a support, wherein a halogen content in the filler is 3.0% to 5.0%.

2. The optical isomer separating filler according to the item 1, wherein hydroxyl groups or amino groups of a polysaccharide are modified with compounds represented by the following formula (I) and/or the following formula (II):

(Chem 1)

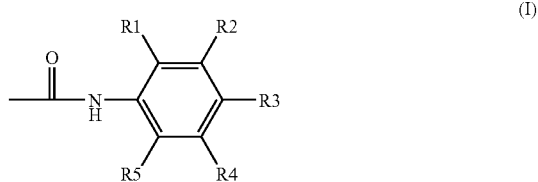

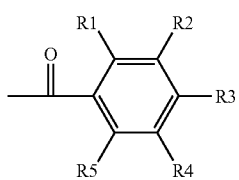

(II)

where at least one of R1 to R5 represents a halogen atom, and the remaining symbols each represent a hydrogen atom, or a linear or branched alkyl group having 1 to 10 carbon atoms.

3. The optical isomer separating filler according to the item 2, wherein the polysaccharide derivative is a cellulose derivative or an amylose derivative.

4. The optical isomer separating filler according to the item 3, wherein the polysaccharide derivative is one of a cellulose tris 3,5-dichlorophenylcarbamate derivative, a cellulose tris 2,4-dichlorophenylcarbamate derivative, a cellulose tris 3,4-dichlorophenylcarbamate derivative, a cellulose tris 2,5-dichlorophenylcarbamate derivative, a cellulose tris 4-fluorophenylcarbamate, a cellulose tris 4-bromophenylcarbamate derivative, a cellulose tris 4-iodophenylcarbamate derivative, an amylose 3,5-dichlorophenylcarbamate derivative, an amylose 2,4-dichlorophenylcarbamate derivative, an amylose 3,4-dichlorophenylcarbamate derivative, an amylose 2,5-dichlorophenylcarbamate derivative, an amylose 4-fluorophenylcarbamate, an amylose 4-bromophenylcarbamate derivative, and an amylose 4-iodophenylcarbamate derivative.

5. The optical isomer separating filler according to any one of the items 1 to 4, wherein a mass of the polysaccharide derivative to a mass of the filler (a percentage of the supported polysaccharide derivative) is 5 to 35.

Effect the Invention

The solvent-resistant optical isomer separating filler of the present invention has a unique separating ability and separating characteristics different from those of conventional products, and can separate optical isomers that cannot be separated with existing optical isomer separating fillers. In addition, the solvent-resistant optical isomer separating filler of the present invention is applicable to various separation conditions; for example, the filler can use a solvent that dissolves a polysaccharide derivative, the solvent having been conventionally unusable as a mobile phase, and further, can use even an acidic or basic solvent that dissolves the polysaccharide derivative as a mobile phase. Accordingly, the filler may be able to separate optical isomers that have been conventionally difficult to separate.

BEST MODE FOR CARRYING OUT THE INVENTION

Figure 1:
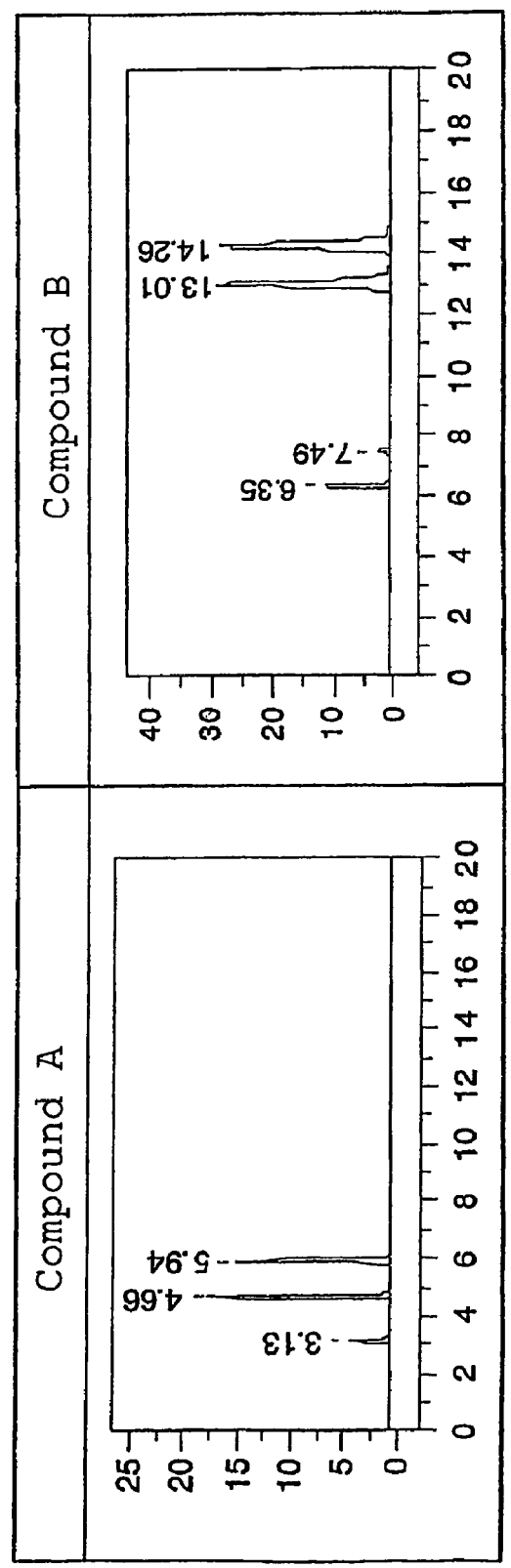
FIG. 1 is a chromatogram for a separation in each of Examples 1 and 2.

Hereinafter, an embodiment of the present invention is described in detail. A commercially available apparatus can be used as an HPLC apparatus.

The polysaccharide to be a raw material of the polysaccharide derivative used in the present invention may be any of a synthetic polysaccharide, a natural polysaccharide, or a modified natural polysaccharide so long as the polysaccharide is optically active. However, the polysaccharide preferably has a highly regulated bonding pattern.

The polysaccharide may include, for example, β-1,4-glucan (cellulose), α-1,4-glucan (amylose, amylopectin), α-1,6-glucan (dextran), β-1,6-glucan (pustulan), β-1,3-glucan (such as cardran, and schizophyllan), α-1,3-glucan, β-1,2-glucan (Crown Gall polysaccharide), β-1,4-galactan, β-1,4-mannan, α-1,6-mannan, β-1,2-fructan (inulin), β-2,6-fructan (levan), β-1,4-xylan, β-1,3-xylan, β-1,4-chitosan, α-1,4-N-acetylchitosan (chitin), pullulan, agarose, alginic acid, α-cyclodextrin, β-cyclodextrin, γ-cyclodextrin, and nigerin, and starches containing amylose.

Of those, preferred are cellulose, amylose, β-1,4-xylan, β-1,4-chitosan, chitin, β-1,4-mannan, inulin, cardran, α-cyclodextrin, β-cyclodextrin, and γ-cyclodextrin, and particularly preferred are cellulose and amylose, with each of which a polysaccharide having a high purity can be easily obtained.

A number average polymerization degree of the polysaccharide (average number of the pyranose or furanose ring contained in one molecule) is 5 or more, and preferably 10 or more. There is no particular upper limitation, the number average molecular degree is preferably 1,000 or less from a viewpoint of easy handling, more preferably 5 to 1,000, still more preferably 10 to 1,000, and particularly preferably 10 to 500.

The polysaccharide derivative used in the present invention is obtained by bonding, to a hydroxyl group or amino group of a polysaccharide, a compound (modifying group) having a functional group capable of reacting with the hydroxyl group or amino group and a functional group that acts on the separation of optical isomers by a known method with an ester bond, urethane bond, ether bond, urea bond, or the like to derivatize (modify) the polysaccharide.

Such a compound having a functional group capable of reacting with the hydroxyl group or amino group of the polysaccharide in which the modifying group is not limited so long as the compound is an isocyanic acid derivative, a carboxylic acid, an ester, an acid halide, an acid amide compound, a halogen compound, an aldehyde, an alcohol, or any other compound having a leaving group; an aliphatic, alicyclic, aromatic, or heteroaromatic compound belonging to any one of them can be used. Such a compound has at least one halogen atom.

Of these polysaccharide derivatives, each being modified with a compound having a functional group that acts on the separation of optical isomers, a carbamate derivative or ester derivative of a polysaccharide, obtained by modifying a hydroxyl group or amino group of the polysaccharide with the compound, represented by the following formula (I) or (II) is particularly preferred.

(Chem 1)

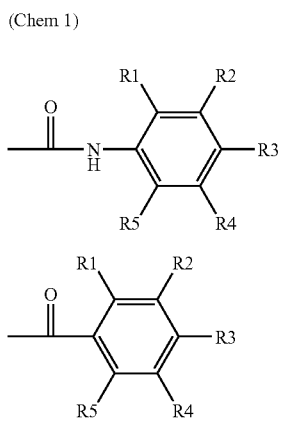

(In the formulae, at least one of R1 to R5 represents a halogen atom, and the remaining symbols each represent a hydrogen atom, or a linear or branched alkyl group having 1 to 10 carbon atoms.)

It should be noted that the polysaccharide derivative of the present invention may be obtained by modifying hydroxyl groups of the polysaccharide with only one kind of a compound represented by the above general formula (I) or (II), or may be obtained by modifying the hydroxyl groups with multiple kinds of compounds each represented by the above general formula (I) or (II).

Of the polysaccharide derivatives obtained by modifying a hydroxyl group or amino group of a polysaccharide with a compound represented by the above general formula (I) or (II), a polysaccharide derivative in which one of R1 to R5 represents a halogen atom and the remaining symbols each represent a hydrogen atom is preferred, and a polysaccharide derivative in which two of R1 to R5 each represent a halogen atom and the remaining symbols each represent a hydrogen atom is more preferred. Of such polysaccharide derivatives, a preferable one is specifically, for example, a cellulose tris 3,5-dichlorophenylcarbamate derivative, a cellulose tris 2,4-dichlorophenylcarbamate derivative, a cellulose tris 3,4-dichlorophenylcarbamate derivative, a cellulose tris 2,5-dichlorophenylcarbamate derivative, a cellulose tris 4-fluorophenylcarbamate, a cellulose tris 4-bromophenylcarbamate derivative, a cellulose tris 4-iodophenylcarbamate derivative, an amylose 3,5-dichlorophenylcarbamate derivative, an amylose 2,4-dichlorophenylcarbamate derivative, an amylose 3,4-dichlorophenylcarbamate derivative, an amylose 2,5-dichlorophenylcarbamate derivative, an amylose 4-fluorophenylcarbamate, an amylose 4-bromophenylcarbamate derivative, or an amylose 4-iodophenylcarbamate derivative.

The ratio at which modifying groups are introduced into the polysaccharide derivative used in the present invention is preferably 3% to 100%, more preferably 15% to 100%, or particularly preferably 30% to 100%. Here, the introduction ratio is defined as described below. That is, when the polysaccharide used in the present invention has only hydroxyl groups, a value obtained by multiplying a ratio of the number of hydroxyl groups modified with a modifying group to the total number of the hydroxyl groups by 100 is the introduction ratio. When the above polysaccharide has only amino groups, a value obtained by multiplying a ratio of the number of amino groups modified with a modifying group to the total number of amino groups by 100 is the introduction ratio. When the above polysaccharide has hydroxyl groups and amino groups, a value obtained by multiplying a ratio of the sum of the number of hydroxyl groups into which a modifying group is introduced and the number of amino groups into which a modifying group is introduced to the sum of the total number of hydroxyl groups and the total number of amino groups by 100 is the introduction ratio.

In the present invention, as a support for carrying the polysaccharide derivative, a porous organic support and a porous inorganic support are exemplified, and preferred is the porous inorganic support. A polymer substance composed of, for example, polystyrene, polyacrylamide, or polyacrylate is suitably used as the porous organic support, and silica, alumina, zirconia, titania, magnesia, glass, kaolin, titanium oxide, a silicate, hydroxyapatite, or the like is suitably used as the porous inorganic support. Silica gel is a particularly preferable support, and silica gel having a particle size of 0.1 μm to 10 μm, or preferably 1 μm to 300 μm, and having an average pore size of 10 Å to 100 μm, or preferably 50 Å to 50,000 Å. The surface of the silica gel is desirably treated in order that an influence of any remaining silanol may be eliminated, but there arises no problem, even when the surface is not treated at all.

The optical isomer separating filler of the present invention is a filler using a polysaccharide derivative coated onto a support as a raw material and having a chemical bond as described below formed in itself, or a filler obtained by chemically bonding a polysaccharide or a polysaccharide derivative and silica gel, a chemical bond between the support and the coated polysaccharide derivative, a chemical bond between the polysaccharide derivatives on the support, a chemical bond using a third component, or a chemical bond formed by, for example, a reaction caused by, for example, the irradiation of the polysaccharide derivative on the support with light, radioactive rays such as γ rays, or an electromagnetic wave such as a microwave or a radical reaction using a radical initiator or the like.

As described in, for example, Patent Document 5 (Japanese Patent Application Laid-open No. Hei 7-138301), the following method is applicable as a specific method of chemically bonding the support and the polysaccharide derivative. After a reducing terminal of a polysaccharide has been chemically bonded to a surface-treated support, the polysaccharide is derivatized so that a target optical isomer separating filler may be obtained.

As described in, for example, the Example of Japanese Patent Application Laid-open No. Hei 8-059702, the following method is applicable as a specific method of chemically bonding the polysaccharide derivatives coated onto the support to one another, a polysaccharide derivative is coated onto a support with its surface inactivated and the molecules of the polysaccharide derivative are crosslinked with a crosslinking agent such as a polyfunctional isocyanate derivative.

As described in, for example, the Example of Patent Document 6 (Japanese Patent Application Laid-open No. 2002-148247), the following method is applicable as a method of chemically bonding the polysaccharide derivative coated onto the support to the support with a third component, a polymerizable polysaccharide derivative into which a polymerizable group such as a vinyl group is introduced and a polymerizable support into which a polymerizable group such as a vinyl group is similarly introduced are copolymerized in the presence of a third component (polymerizable monomer) having a vinyl group or the like.

As described in, for example, the Example of Patent Document 4 (Japanese Patent Translation Publication No. Hei 11-510193), the following method is applicable as a method of chemically bonding the polysaccharide derivative coated onto the support to the support by irradiation with light, after a polysaccharide derivative has been coated onto a support, the resultant is irradiated with light from an immersion mercury lamp so that the polysaccharide derivative may be photochemically crosslinked with the support.

As described in, for example, Japanese Patent Application Laid-open No. 2004-167343, the following method is applicable as a method of chemically bonding the polysaccharide derivative coated onto the support to the polysaccharide derivative and/or the support by irradiation with radioactive rays such as γ rays or an electromagnetic wave such as a microwave, after a polysaccharide derivative has been coated onto a surface-treated support, the resultant is irradiated with γ rays so that the polysaccharide derivative may be chemically bonded to the polysaccharide derivative and/or the support.

Alternatively, for example, the following method is also applicable as a method of chemically bonding the polysaccharide derivative coated onto the support to the support, a polysaccharide derivative obtained by introducing alkoxysilyl groups into a part of the hydroxyl groups or amino groups of a polysaccharide is coated onto a support, and crosslinks are formed with the alkoxysilyl groups in a proper solvent so that the polysaccharide derivative may be chemically bonded to the support.

In the optical isomer separating filler in which the polysaccharide derivative is chemically bonded onto the support as described above, the percentage of the supported polysaccharide derivative (%) of the polysaccharide derivative on the support (ratio of the amount (parts by mass) of the polysaccharide derivative in 100 parts by mass of the optical isomer separating filler) is preferably 1 to 50%, more preferably 5 to 35%, or particularly preferably 5 to 20%.

A halogen content in the optical isomer separating filler according to the present invention obtained as described above is preferably 3.0% to 5.0%, or more preferably 3.4% to 4.5%. A filler having a halogen content of less than 3.0% may not favorably separate optical isomers. In addition, a filler having a halogen content of more than 5.0% involves the following drawback, the number of theoretical plates of the peak of a chromatogram to be obtained reduces, so a reduction in separation efficiency is observed.

The optical isomer separating filler having a halogen content in a specific range defined in the present invention can be obtained by adjusting, for example, the introduction ratio of the modifying groups in the polysaccharide derivative and the percentage of the supported polysaccharide derivative of the polysaccharide derivative on a support.

EXAMPLES

Examples are shown below. Needless to say, the scope of the present invention is not limited to these examples. It should be noted that a halogen content in each of the examples was measured by combustion ion chromatography (combustion conditions: tube furnace combustion temperature: 1,000 to 1,100° C., combustion tube: a quartz glass tube, absorbing solution: an aqueous solution of hydrogen peroxide, ion chromatographic analysis: separating column: a general-purpose anion analysis column (such as an AS-12 manufactured by Dionex Corporation), detector: an electric conductivity detector, mobile phase: an alkaline aqueous solution such as an aqueous solution of 3.0 mM of $K_2CO_3$ and 0.3 mM of $KHCO_3$).

Example 1

Cellulose tris(3,5-dichlorophenylcarbamate) was produced in accordance with a known method (such as the method described in Synthesis Example 1 of Patent Document 3 (Japanese Patent Application Laid-open No. Sho 61-233633) with a change that 3,5-dichlorophenyl isocyanate was used instead of 3,4-dichlorophenyl isocyanate), and 3.0 g of cellulose tris(3,5-dichlorophenylcarbamate) thus obtained were dissolved in 30 mL of tetrahydrofuran (THF). The solution of cellulose tris(3,5-dichlorophenylcarbamate) in THF was uniformly coated onto 15 g of silica gel with its surface treated with an aminosilane (silica gel identical to that used in Example 1 of Patent Document 4 (Japanese Patent Translation Publication No. Hei 11-510193)). After that, the THF was removed by distillation.

10 g of the substance obtained by coating the support with the polysaccharide derivative by the above steps were suspended in a mixed solvent, and the suspension was stirred in the same manner as in Example 1 of Patent Document 4 (Japanese Patent Translation Publication No. Hei 11-510193). The suspension was irradiated with light from an immersion mercury lamp (Philips, HPK-125 kW, coated with quartz) for 10 minutes. The suspension was filtered and washed with methanol, whereby an optical isomer separating filler in which the polysaccharide derivative was chemically bonded onto the support was obtained. Table 1 shows a chlorine content after the resultant filler has been washed with THF.

Example 2

5.0 g (30.8 mmol) of cellulose were dissolved in 150 mL of a solution of lithium chloride in N,N-dimethylacetamide. 75 mL of pyridine and 14.4 g (76.6 mmol) of 3,5-dichlorophenyl isocyanate were added to the solution, and the mixture was subjected to a reaction at 80° C. for 6 hours. After that, 0.61 g (2.5 mmol) of 3-isocyanatepropyltriethoxysilane was added to the mixture, and the whole mixture was subjected to a reaction for an additional 16 hours. After that, 14.5 g (76.6 mmol) of 3,5-dichlorophenyl isocyanate were added to the resultant mixture, and the whole mixture was subjected to a reaction for an additional 7 hours. A pyridine-soluble portion was dropped into methanol and was recovered as an insoluble portion. After that, the portion was dried in a vacuum, whereby a cellulose derivative having alkoxysilyl groups introduced into its part was obtained. $^1H$ NMR results showed that the introduction ratio of 3,5-dichlorophenyl isocyanate was 98.2%, and the introduction ratio of the alkoxysilyl groups was 1.8%.

2.5 g of the resultant cellulose derivative were dissolved in 20 mL of tetrahydrofuran (THF) and the solution of the alkoxysilyl group-introduced cellulose tris(3,5-dichlorophenylcarbamate) in THF was uniformly coated onto 7.5 g of silica gel with its surface treated with an aminosilane (silica gel identical to that used in Example 1 of Patent Document 4 (Japanese Patent Translation Publication No. Hei 11-510193)). After that, the THF was removed by distillation.

6.0 g of the substance obtained by coating the support with the polysaccharide derivative by the above steps were dispersed in ethanol/water/chlorotrimethylsilane (55 mL/14 mL/0.9 mL), and the mixture was subjected to a reaction for 10 minutes while being boiled in an oil bath at 110° C. so that the polysaccharide derivative might be immobilized on silica gel. The resultant mixture was washed with methanol and dried in a vacuum, whereby an optical isomer separating filler in which the cellulose carbamate derivative was immobilized was obtained. Table 1 shows the chlorine content after the resultant filler has been washed with THF.

Comparative Example 1

1.0 g of cellulose tris(3,5-dichlorophenylcarbamate) produced by the same approach as that of Example 1 was dissolved in 8.0 mL of tetrahydrofuran (THF). The solution of cellulose tris(3,5-dichlorophenylcarbamate) in THF was uniformly coated onto 10 g of silica gel with its surface treated with an aminosilane. After that, the THF was removed by distillation.

10 g of the substance obtained by coating the support with the polysaccharide derivative by the above steps were suspended in a mixed solvent, and the mixture was stirred in the same manner as in Example 1. The suspension was irradiated with light from an immersion mercury lamp (Philips, HPK-125 kW, coated with quartz) for 8.0 minutes. The suspension was filtered and washed with methanol, whereby an optical isomer separating filler in which the polysaccharide derivative was chemically bonded onto the support was obtained. Table 1 shows the chlorine content after the resultant filler has been washed with THF.

Comparative Example 2

10 g of a substance in which cellulose was chemically bonded to a support were synthesized with reference to the method described in Example 1 (paragraphs 0071 to 0075) of Patent Document 5 (Japanese Patent Application Laid-open No. Hei 7-138301); provided that the substance in which cellulose was chemically bonded to the support was obtained with the loading of cellulose in this case set to be twice as large as that described in the patent document. 5 g of the resultant cellulose-bonded silica gel were suspended in a mixed solvent of N,N-dimethylacetamide and pyridine. 15 g of 3,5-dichlorophenyl isocyanate were added to the suspension, and the mixture was subjected to a reaction at 80° C. for 48 hours. The resultant suspension was filtered and washed with methanol, whereby an optical isomer separating filler in which the polysaccharide derivative was chemically bonded to the support was obtained. Table 1 shows a chlorine content after the resultant filler has been washed with THF.

Comparative Example 3

1.0 g of the cellulose carbamate derivative into which alkoxysilyl groups were introduced obtained by the method of Example 2 was dissolved in 7.0 mL of tetrahydrofuran (THF). The solution of the alkoxysilyl group-introduced cellulose tris(3,5-dichlorophenylcarbamate) in THF was uniformly coated onto 9.0 g of silica gel with its surface treated with an aminosilane (silica gel identical to that used in Example 1 of Patent Document 4 (Japanese Patent Translation Publication No. Hei 11-510193)). After that, THF was removed by distillation.

6.0 g of the substance obtained by coating the support with the polysaccharide derivative by the above steps were dispersed in ethanol/water/chlorotrimethylsilane (55 mL/14 mL/0.9 mL), and the mixture was subjected to a reaction for 10 minutes while being boiled in an oil bath at 110° C. so that the polysaccharide derivative might be immobilized on silica gel. The resultant filler was washed with methanol and dried in a vacuum, whereby an optical isomer separating filler in which the cellulose carbamate derivative was immobilized was obtained. Table 1 shows a chlorine content after the resultant filler has been washed with THF.

Comparative Example 4

5.0 g (30.8 mmol) of cellulose were dissolved in 100 mL of a solution of lithium chloride in N,N-dimethylacetamide. 53 mL of pyridine and 17.8 g (86.4 mmol) of 3,5-dichlorophenyl isocyanate were added to the solution, and the mixture was subjected to a reaction at 80° C. for 6 hours. After that, 0.96 g (3.9 mmol) of 3-isocyanatepropyltriethoxysilane was added to the mixture, and the whole mixture was subjected to a reaction for an additional 16 hours. After that, 13.2 g (64.2 mmol) of 3,5-dichlorophenyl isocyanate were added to the resultant mixture, and the whole mixture was subjected to a reaction for an additional 7 hours. A pyridine-soluble portion was dropped into methanol and was recovered as an insoluble portion. After that, the portion was dried in a vacuum, whereby a cellulose carbamate derivative having alkoxysilyl groups introduced into its part was obtained.

$^1$H NMR results showed that the introduction ratio of 3,5-dichlorophenyl isocyanate was 97.6%, and the introduction ratio of the alkoxysilyl groups was 2.4%. 3.5 g of the resultant cellulose carbamate derivative were dissolved in 30 mL of tetrahydrofuran (THF), and the solution of the alkoxysilyl group-introduced cellulose tris(3,5-dichlorophenylcarbamate) in THF was uniformly coated onto 6.5 g of silica gel with its surface treated with an aminosilane (silica gel identical to that used in Example 1 of Patent Document 4 (Japanese Patent Translation Publication No. Hei 11-510193)). After that, the THF was removed by distillation.

5 g of the substance obtained by coating the support with the polysaccharide derivative by the above steps were dispersed in ethanol/water/chlorotrimethylsilane (55 mL/14 mL/0.9 mL), and the mixture was subjected to a reaction for 10 minutes while being boiled in an oil bath at 110° C. so that the polysaccharide derivative might be immobilized on silica gel. The resultant filler was washed with methanol and dried in a vacuum, whereby an optical isomer separating filler in which the cellulose carbamate derivative was immobilized was obtained. Table 1 shows the chlorine content after the resultant filler has been washed with THF.

TABLE 1

|  | Chlorine content |
| --- | --- |
| Example 1 | 3.4% |
| Example 2 | 4.5% |
| Comparative Example 1 | 2.6% |
| Comparative Example 2 | 5.2% |
| Comparative Example 3 | 1.5% |
| Comparative Example 4 | 6.8% |

Applied Examples

Figure 2:
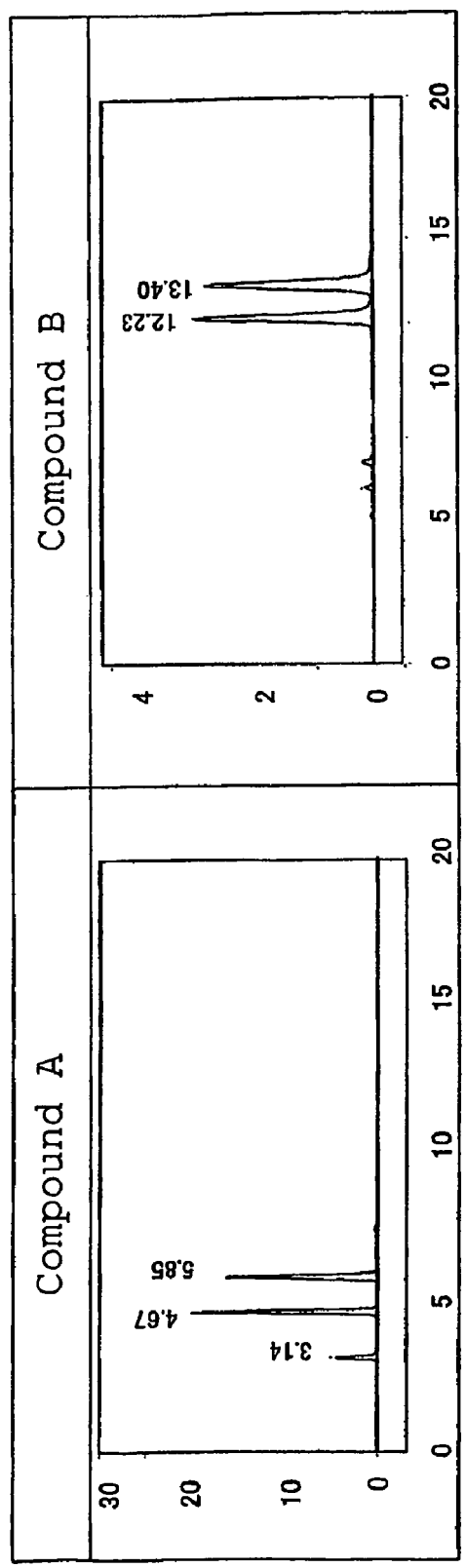
FIG. 2 is a chromatogram obtained in Example 2.
Figure 3:
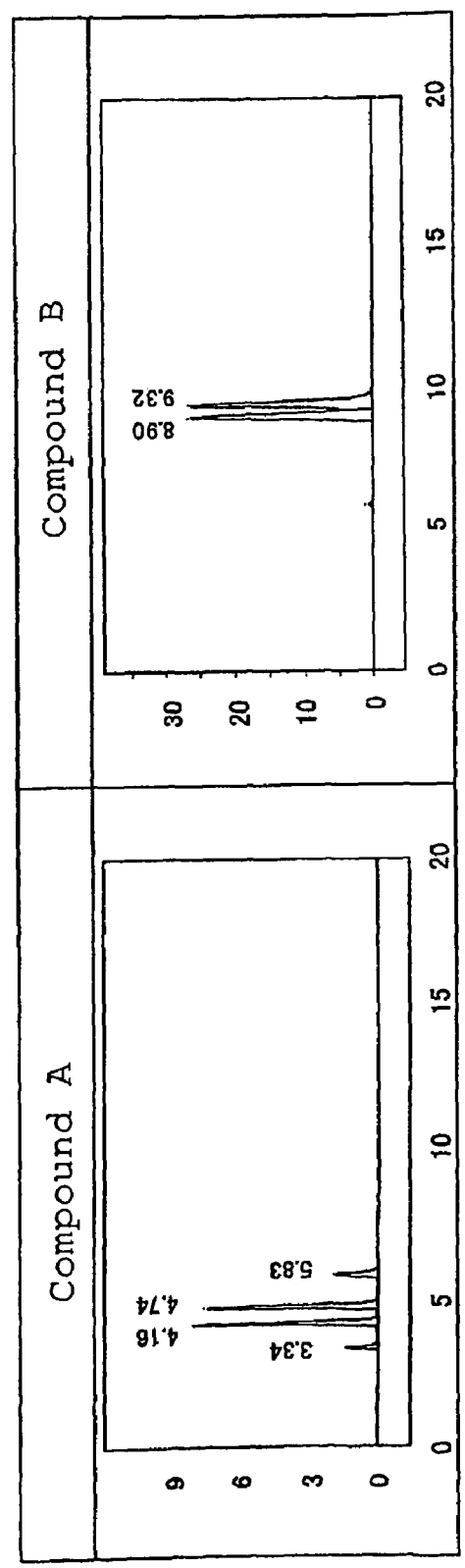
FIG. 3 is a chromatogram obtained in Comparative Example 1.
Figure 4:
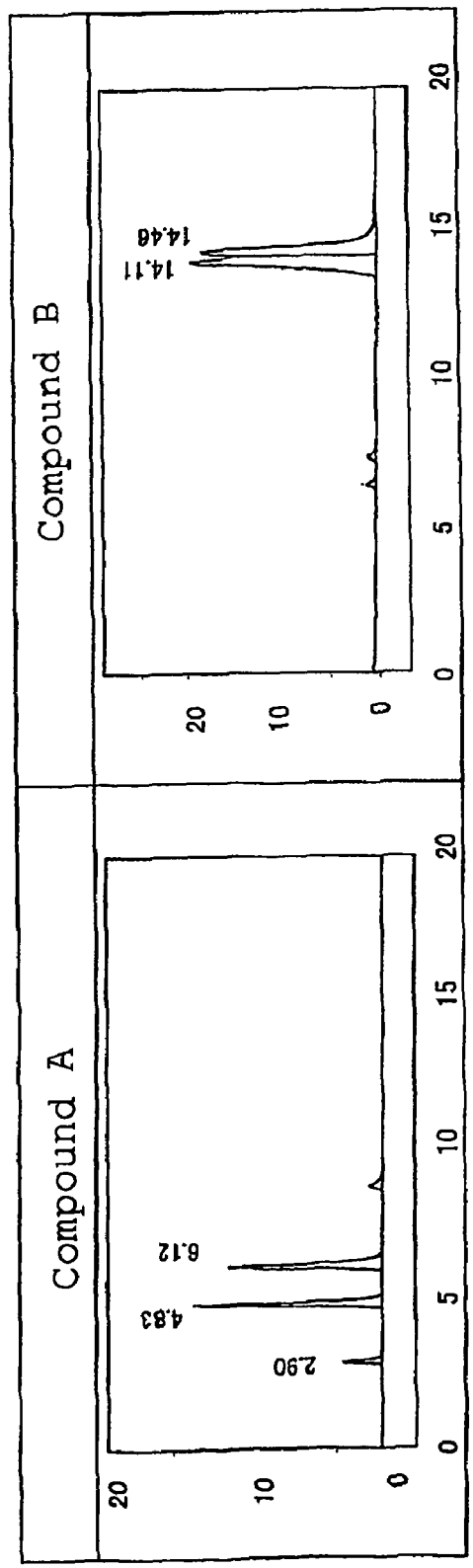
FIG. 4 is a chromatogram obtained in Comparative Example 2.
Figure 5:
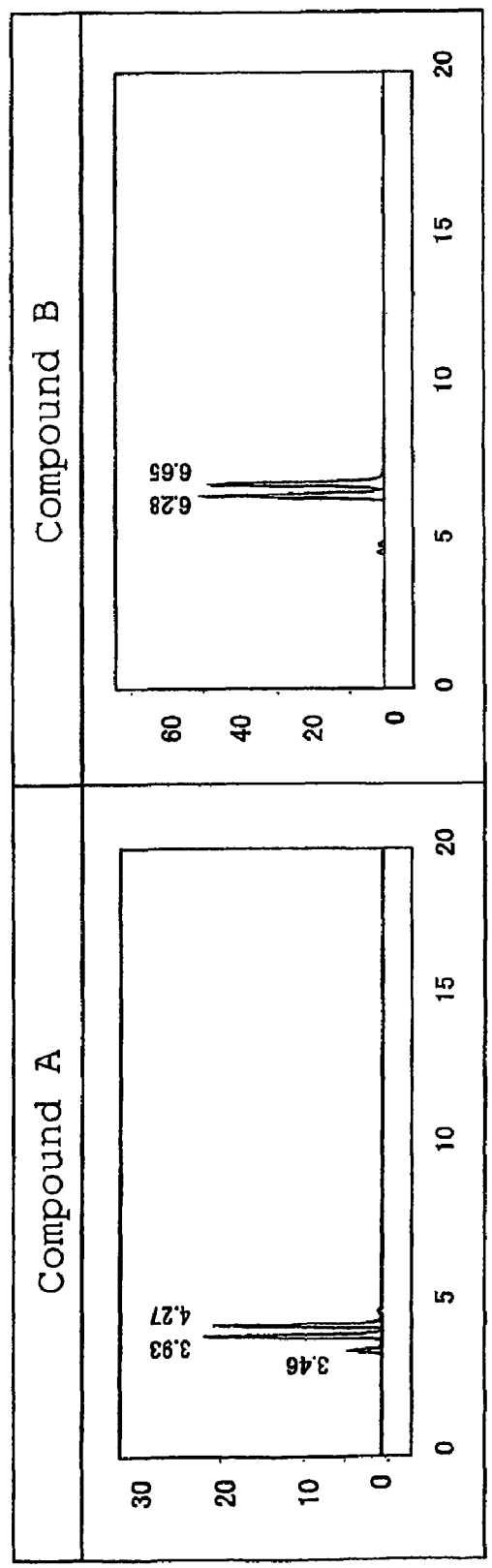
FIG. 5 is a chromatogram obtained in Comparative Example 3.
Figure 6:
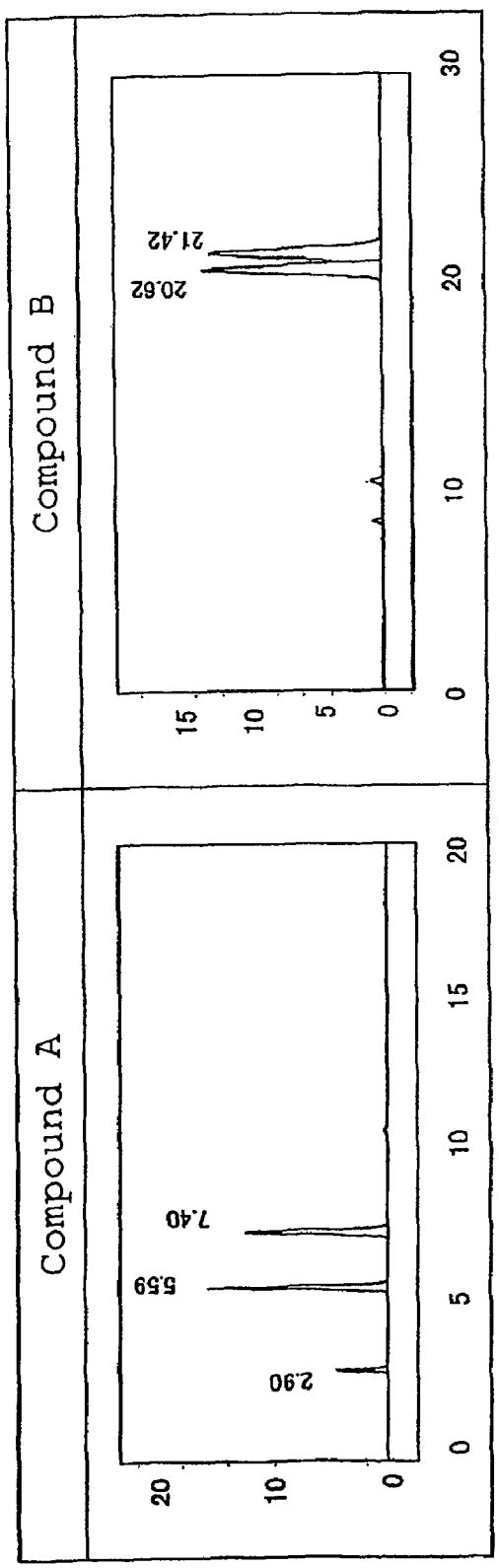
FIG. 6 is a chromatogram obtained in Comparative Example 4.

The optical isomer separating fillers produced in Examples 1 and 2 were each loaded into a stainless column having a diameter of 0.46 mm and a length of 25 cm by a slurry method, and an analysis test for the following racemic bodies (Compounds A and B) was performed with a high performance liquid chromatography (HPLC) apparatus. Table 2 shows the results. In addition, FIGS. 1 to 6 illustrate the respective chromatograms in the applied examples. It should be noted that conditions for the analysis by HPLC were as follows: a mobile phase:hexane/2-propanol of 90/10 (volume ratio), a flow rate: 1.0 ml/min, a column temperature: 25° C., and a detection wavelength: 254 nm.

In the table, α represents a separation factor, and is determined from capacity ratios represented by k1' and k2'. The capacity ratios are determined from the following equations (1) and (2) where t0 represents the time period for which tri-tert-butylbenzene passes through the column, and t1 and t2 each represent a time period needed for the elution of a separated optical isomer (elution time at each of the first and second peaks) (where t1<t2). In addition, the separation factor α is determined from the following equation (3) by using the capacity ratios.

$$k1'=(t1-t0)/t1 \quad (1)$$

$$k2'=(t2-t0)/t0 \quad (2)$$

$$\alpha=k2'/k1' \quad (3)$$

Further, Rs in the table represents a resolution of the first peak and the second peak, and is determined from the following equation (4).

$$Rs=2(t2-t1)/(W1+W2) \quad (4)$$

In the equation, W1 represents the peak width of the first peak on a baseline, and W2 represents the peak width of the second peak on the baseline.

TABLE 2

(Chem 2)

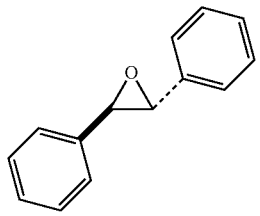

Compound A

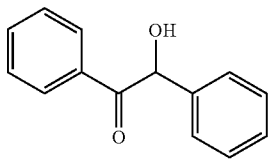

Compound B

| | Compound A | | | Compound B | | |
|---|---|---|---|---|---|---|
| | α value | Rs value | Separation result | α value | Rs value | Separation result |
| Example 1 | 1.84 | 7.74 | Baseline separation | 1.13 | 2.90 | Baseline separation |
| Example 2 | 1.77 | 6.01 | Baseline separation | 1.13 | 2.39 | Baseline separation |
| Comparative Example 1 | 1.71 | 2.98 | Baseline separation | 1.08 | 1.15 | Partial separation |
| Comparative Example 2 | 1.67 | 5.49 | Baseline separation | 1.04 | 0.70 | Partial separation |
| Comparative Example 3 | 1.72 | 2.26 | Baseline separation | 1.13 | 1.61 | Partial separation |
| Comparative Example 4 | 1.67 | 7.89 | Baseline separation | 1.05 | 0.95 | Partial separation |

INDUSTRIAL APPLICABILITY

The optical isomer separating filler of the present invention has a solvent resistance and an optical resolving ability comparable to or higher than those of existing optical isomer separators. Further, the filler shows an optical resolving ability higher than those of the existing optical isomer separating fillers for some kinds of optical isomers. Therefore, the filler can separate optical isomers that have been conventionally unable to be resolved, and the filler can be utilized with each separated optical isomer in, for example, the development of a new drug.

The invention claimed is:

1. An optical isomer separating filler comprising a polysaccharide derivative
chemically bonded onto a support, wherein a halogen content in the filler is 3.0% to 5.0%,
wherein the polysaccharide derivative is one of
a cellulose tris 3,5-dichlorophenylcarbamate derivative,
a cellulose tris 2,4-dichlorophenylcarbamate derivative,
a cellulose tris 3,4-dichlorophenylcarbamate derivative,
a cellulose tris 2,5-dichlorophenylcarbamate derivative,
a cellulose tris 4-fluorophenylcarbamate,
a cellulose tris 4-bromophenylcarbamate derivative,
a cellulose tris 4-iodophenylcarbamate derivative,
an amylose 3,5-dichlorophenylcarbamate derivative,
an amylose 2,4-dichlorophenylcarbamate derivative,
an amylose 3,4-dichlorophenylcarbamate derivative,
an amylose 2,5-dichlorophenylcarbamate derivative,
an amylose 4-fluorophenylcarbamate,
an amylose 4-bromophenylcarbamate derivative, and
an amylose 4-iodophenylcarbamate derivative.

2. The optical isomer separating filler according to claim 1, wherein a mass ratio of the polysaccharide derivative to the optical isomer separating filler is 5 to 35%.

* * * * *